(12) United States Patent
Tenerz et al.

(10) Patent No.: US 7,011,678 B2
(45) Date of Patent: Mar. 14, 2006

(54) BIODEGRADABLE STENT

(75) Inventors: Lars Tenerz, Uppsala (SE); Pär von Malmborg, Uppsala (SE); Torbjörn Mathisen, Älvsjö (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/501,536

(22) PCT Filed: Dec. 18, 2002

(86) PCT No.: PCT/SE02/02365

§ 371 (c)(1),
(2), (4) Date: Jul. 16, 2004

(87) PCT Pub. No.: WO03/063733

PCT Pub. Date: Aug. 7, 2003

(65) Prior Publication Data

US 2005/0010279 A1  Jan. 13, 2005

Related U.S. Application Data

(60) Provisional application No. 60/352,581, filed on Jan. 31, 2002.

(30) Foreign Application Priority Data

Jan. 31, 2002 (SE) .................................... 0200293

(51) Int. Cl.
    *A61F 2/06* (2006.01)
(52) U.S. Cl. ..................................... 623/1.15; 623/1.16
(58) Field of Classification Search .............. 623/1.12, 623/1.22, 1.38, 1.39–1.48
See application file for complete search history.

(56) References Cited

U.S. PATENT DOCUMENTS

| | | | |
|---|---|---|---|
| 5,160,341 A | 11/1992 | Brenneman et al. | |
| 5,306,286 A | 4/1994 | Stack et al. | |
| 5,676,685 A | 10/1997 | Razavi | |
| 5,799,384 A | 9/1998 | Schwartz et al. | |
| 5,957,975 A | 9/1999 | Lafont et al. | |
| 5,968,970 A | 10/1999 | Bley et al. | |
| 6,071,308 A * | 6/2000 | Ballou et al. | 623/1.15 |
| 6,106,548 A * | 8/2000 | Roubin et al. | 623/1.15 |
| 6,159,142 A | 12/2000 | Alt | |
| 6,192,271 B1 | 2/2001 | Hayman | |
| 6,193,744 B1 * | 2/2001 | Ehr et al. | 623/1.16 |
| 6,206,195 B1 | 3/2001 | Cheng | |
| 6,241,691 B1 * | 6/2001 | Ferrera et al. | 600/585 |
| 6,287,332 B1 | 9/2001 | Bolz et al. | |
| 2002/0004060 A1 | 1/2002 | Heublein et al. | |

FOREIGN PATENT DOCUMENTS

| | | |
|---|---|---|
| DE | 199 45 049 A1 | 3/2001 |
| DE | 101 25 999 A1 | 11/2002 |
| WO | WO 01/89417 A1 | 11/2001 |

* cited by examiner

Primary Examiner—Corrine McDermott
Assistant Examiner—Hieu Phan
(74) Attorney, Agent, or Firm—Foley & Lardner LLP

(57) ABSTRACT

Expandable stent for insertion into a body passage having a mesh structure of interconnecting portions (6) joined together by joining portions (5). The stent, when inserted into said body passage, is adapted to dissolve into smaller parts, wherein the joining portions dissolve faster than the interconnecting portions. In a preferred embodiment the joining portions are made from a first material and the interconnecting portions are made from a second material different from said first material, wherein the first material dissolves faster than said second material.

39 Claims, 4 Drawing Sheets

BIODEGRADABLE STENT

RELATED APPLICATION

This application is a 371 of PCT/SE02/02365, filed Dec. 18, 2002, which claims benefit of 60/352,581, filed on Jan. 31, 2002.

FIELD OF THE INVENTION

The present invention relates to an expandable stent according to the preamble of the independent claim.

The present invention relates generally to the field of expandable stents for insertion into vessels in the body, and particularly to dissolvable stents being made of a metal that dissolves by corrosion inside the body vessel and to disintegrating stents being made of two metals with different electrochemical potentials, thereby forming a galvanic element in which an electrochemical reaction occurs that consumes the metal having the lower electrochemical potential.

BACKGROUND OF THE INVENTION

A number of different stents have been proposed for the stenting of a blood vessel that has been occluded. A widely used type of stent consists of an expandable metal mesh. This type of stent may be further divided into self-expanding stents and non-self-expanding stents.

The self-expanding stents can be made of a mesh material that changes to a larger-size configuration upon heating to body temperature. Examples of stents of this type may be found in U.S. Pat. No. 6,071,308. Other self-expanding mesh stents are made of a resilient material, which can be flexed down into a small diameter tube and held in place in this configuration until it is released, at which time the mesh expands to the larger configuration.

The non-self-expanding stents are often expanded by use of an inflatable balloon, which is placed inside the mesh being in the small diameter configuration and which is then inflated, thereby expanding the mesh to the large diameter configuration. The balloon itself is then deflated for removal, while the metal mesh is left in the expanded configuration. For examples of non-self-expanding stents, see U.S. Pat. No. 5,799,384 and the international application WO-0189417.

Some of these expandable metal mesh stents are combined with an expandable polymer layer, which may be positioned on the inside of the expandable mesh, on the outside of the expandable mesh, within the interstices of the expandable mesh, or any combination of inside, outside and within the interstices of the expandable mesh stent. A stent of this type is, for example, shown in U.S. Pat. No. 5,968,070, wherein the polymer layer may consist of expanded polytetrafluoroethylene (PTFE). As disclosed in, for example, U.S. Pat. No. 5,160,341, it is also possible to use a polymer layer made of a resorbable polymer, such as polylactic acid homopolymers, polyglycolic acid homopolymers, or copolymers of polylactic acid and polyglycolic acid.

One advantage with expandable metal mesh stents is that their small diameter in the pre-expanded state allows easy insertion into narrow vessels. However, after the expansion, the metal mesh stents are difficult to remove since tissue in-growth occurs over time, and, in practise, the stents are normally left inside the blood vessel. The main complication associated with the stenting of a stenosis in a blood vessel is the risk of having a restenosis, in which case a new stenosis develops at the same position as the first one, i.e. a new stenosis is growing inside the inserted stent. Several types of stents have been suggested to handle this severe problem, including drug-delivering stents and radioactive stents. Examples of drug-delivering stents may be found in U.S. Pat. No. 6,206,195, while examples of stents for radiotherapy may be found in U.S. Pat. No. 6,192,271.

Nevertheless, there is still a substantial risk of having a restenosis following the stenting of a coronary artery. In this case, a second stent is normally inserted and expanded inside the first one, which obviously reduces the diameter of the second stent in its expanded configuration as well as the inner diameter of the re-stented blood vessel.

Further, when a stent is placed permanently inside a coronary artery, the continuous stress from the beating of the heart may cause the wall and edges of the stent to damage the vessel wall. This damage can lead to arterial rupture or aneurysm formation. Also, a stent adapted to be permanently implanted within a blood vessel is continuously exposed to the flow of blood inside the vessel, which may lead to thrombus formation within the blood vessel. Stents made of absorbable materials (see e.g. U.S. Pat. No. 5,306,286) have been proposed in order to overcome these problems. A disadvantage with such stents is that they are difficult to expand, i.e. they are of the self-expandable type. They have also a limited capability to withstand the compressive pressure exerted by the blood vessel in their expanded configuration.

A biodegradable polymeric stent having a programmed pattern of in vivo degradation is disclosed in U.S. Pat. No. 5,957,975. The stent comprises a substantially cylindrical element having two open ends and a plurality of different regions where each region has a desired in vivo lifetime.

And finally, U.S. Pat. No. 6,287,332 discloses an implantable, bioresorbable vessel wall support, in particular a coronary stent, that comprises a combination of metal materials which dissolves in the human body without any harmful effects on the person that wears the implant. The combination of metal materials can be an alloy or a local galvanic element. No specific structure of the stent is disclosed in U.S. Pat. No. 6,287,332.

It would therefore be desirable to provide a stent that combines the expandability and structural integrity of the metal mesh stents with the advantages of the absorbable stents. Such a stent would allow easy insertion into the blood vessel and yet being expandable enough to expand the blood vessel to the desired volume. The stent should also avoid the complications associated with permanently implanted stents by becoming dissolved or disintegrated. A stent having these characteristics would allow stenting of a restenosis, with the final inner diameter of the re-stented blood vessel being the same as after the first stenting operation.

Furthermore, a blood vessel provided with a stent in the longer term will loose some of its elasticity. An absorbable stent that relatively quickly and in a controllable manner looses its mechanical strength would enable, in an advantageous way, the blood vessel to rapidly regain its elasticity.

SUMMARY OF THE INVENTION

The object of the present invention is to provide an expandable stent, which dissolves or disintegrates inside a blood vessel after a predefined time.

In a first embodiment, the stent comprises a mesh made of a metal that dissolves by corrosion in the environment prevailing within the blood vessel.

In a second embodiment, the metal mesh is made of at least two metals having different electrochemical potentials, thereby forming an active galvanic element. In the galvanic element, an electrochemical reaction occurs, which consumes the metal having the lower electrochemical potential. If the joints of the metal mesh are made of the metal having the lower electrochemical potential, these joints will dissolve, which leaves the rest of the mesh in a disintegrated configuration.

In a third embodiment, a more generalised stent, is disclosed, having a mesh structure of interconnecting parts joined together by joining parts that, when inserted into said body passage, is adapted to dissolve into smaller parts, wherein the joining parts dissolves faster than the interconnecting parts. Preferably, the joining parts and the interconnecting parts are made from a first and a second material, respectively, wherein the first material dissolves faster than the second material.

The above-mentioned object is achieved by an expandable stent and by a method according to the independent claims.

Preferred embodiments are defined in the dependent claims.

DETAILED DESCRIPTION OF THE PREFERRED EMBODIMENTS

Figure 1:
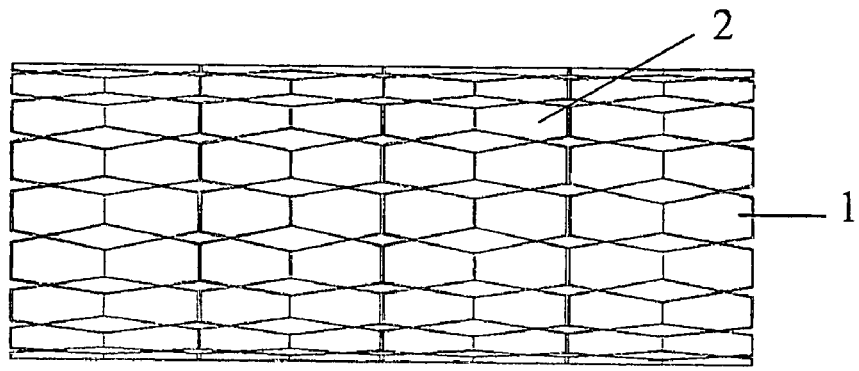
FIG. 1 shows a first embodiment of an expandable metal mesh stent according to the invention.

FIG. 1 illustrates a first embodiment of an inventive stent. In FIG. 1, a stent 1 comprises a mesh 2 made of metal that corrodes in the environment prevailing inside a vessel. By choosing a suitable metal, it is possible to control the time elapsed until the stent is dissolved by corrosion inside the vessel. Obviously, this time depends on the physiological and chemical characteristics of both the vessel itself and the fluid flowing inside the vessel as well as for how long time it is necessary to support the stented vessel. A perhaps natural choice of metal would in this case be iron, or possibly an alloy of iron and a small amount of chromium or nickel in order to make the stent more resistant to corrosion, i.e. prolong the time before the stent is dissolved inside the vessel. In practise, the choice of metal or alloy may be tailored to the actual application.

Figure 2:
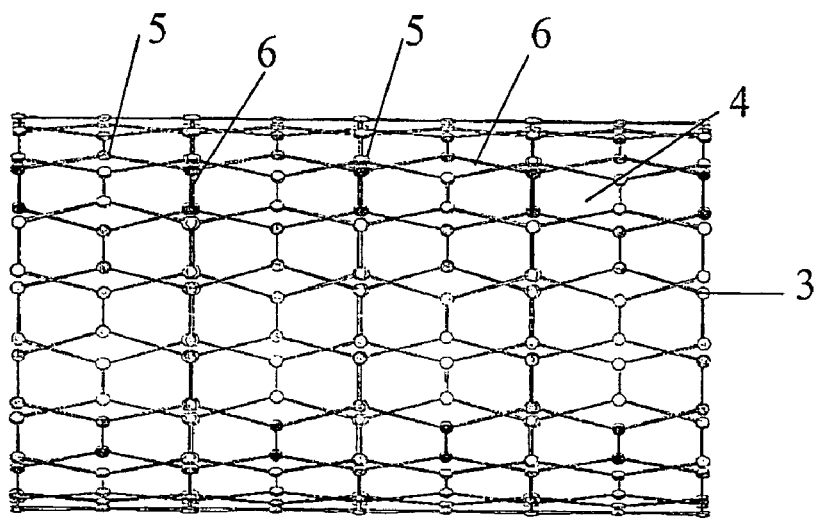
FIG. 2 shows a second embodiment of an expandable metal mesh stent according to the invention.
Figure 3:
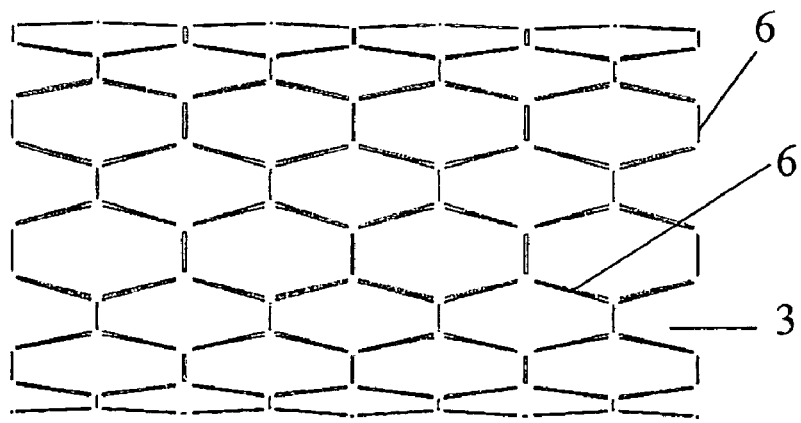
FIG. 3 shows the stent of FIG. 2 in a disintegrated state.

A second embodiment of an inventive stent is illustrated in FIG. 2. Here, a stent 3 comprises a metal mesh 4, which comprises two component parts, joining 5 and interconnecting portions 6. If the joints 5 are made of metal having a lower electrochemical potential than the metal of the interconnecting portions 6, an active galvanic element is created, with the fluid inside the vessel acting as an electrolyte. This galvanic element drives an electrochemical process, in which the metal having the lower electrochemical potential is consumed, which, in this case, means that the joining portions 5 of the mesh 4 are dissolved, thereby leaving the mesh 4 in a disintegrated configuration. This disintegrated configuration is shown in FIG. 3. As is well known, the kinetics of corrosion reactions may in actual practise differ from that predicted by electrochemical potentials in standard electrochemical series. When deciding metal combinations, one must therefore also take into account the characteristics of the vessel in question.

In the second embodiment described above, the joining portions 5 could, for example, consist of zinc while the interconnecting portions 6 consist of iron. With this material combination, the whole stent 3 would eventually be dissolved since the interconnecting portions 6 would dissolve by corrosion when the joining portions 5 have been consumed in the electrochemical process of the galvanic element. Another possibility is to make the mesh 4 of a first metal, such as iron, and then provide a layer of a second metal, such as gold, having a higher electrochemical potential at the joining portions 5. This configuration would create an electrochemical process in which the first metal (e.g. iron) is consumed beneath the layer of the second metal (e.g. gold). This combination would yield the same disintegrated configuration as shown in FIG. 3, the only difference being the small remainders of the second metal at the joining portions 5. In practise, the remaining amounts of the second metal can be made negligible small. As before, the specific materials and material combinations can be tailored to the desired time before disintegration of the stent. It is, of course, also possible to provide the two metals at other positions than the joints and straight portions of the mesh, which would leave the disintegrated stent in some other configuration than the one shown in FIG. 3. Further, the metal mesh could be made of more than two metals with different electrochemical potentials. If, for example three metals were used, two different galvanic elements would be created, which provides additional possibilities to adapt the disintegrations rates of the metal meshes as well as the disintegrated configurations to the specific application conditions.

A more general third embodiment of the present invention is illustrated by FIGS. 2 and 3, and by FIGS. 6a–6c and 7a–7c.

By using the same reference signs, in FIGS. 6a–6c and 7a–7c, as in FIG. 2 the generalised expandable stent 3 comprises a mesh structure 4 of interconnecting portions 6 joined together by joining portions 5.

According to this third embodiment the joining portions are made from a first material and the interconnecting portions are made from a second material different from said first material, wherein the first material dissolves faster than said second material.

By using this mesh structure the stent dissolves in such a way that the longitudinal structural integrity initially is decreased and that the longitudinal structural integrity decreases faster than the radial structural integrity decreases. The radial structural integrity is related to the forces exerted by the stent towards the body passage wall. Thereby the flexibility of the stent in the longitudinal direction of the body passage gradually increases but the support of the body passage wall remains more or less unchanged for a longer time.

FIGS. 6a–6c and 7a–7c illustrate the degrading procedure.

Figure 6A:
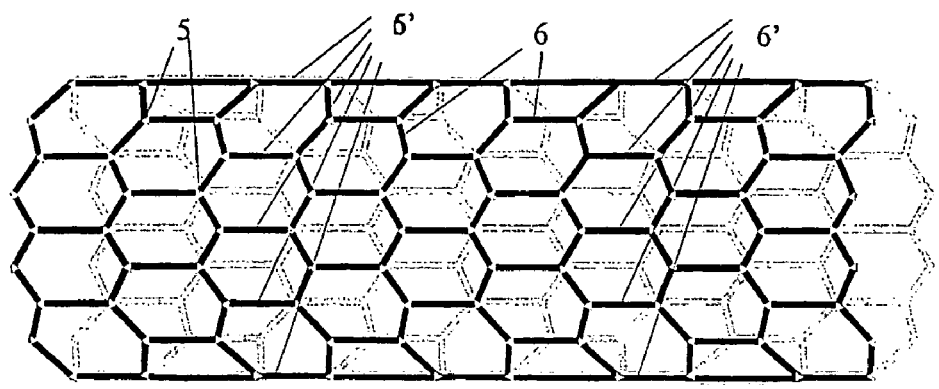
FIG. 6a illustrates a modification of a third embodiment of the present invention.
Figure 6B:
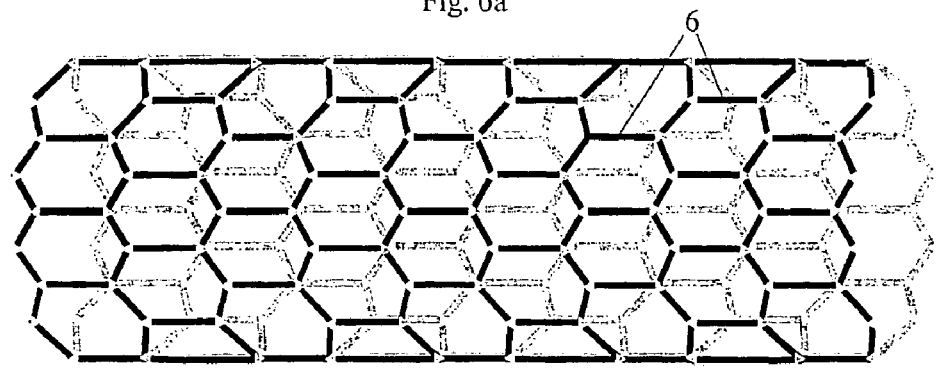
FIGS. 6b and 6c illustrate the third embodiment of the present invention.
Figure 6C:
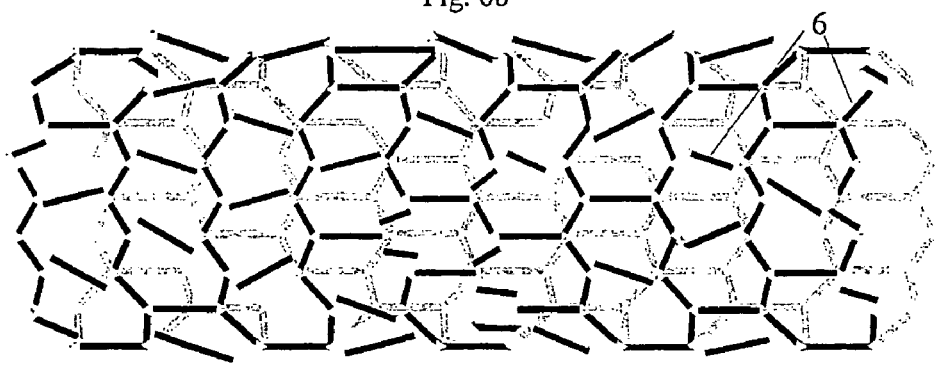

In FIGS. 6a–6c a stent having a mesh structure comprising hexagonal cells is illustrated.

In a modified third embodiment illustrated in FIG. 6a some of the interconnecting portions 6' are made from the same material as the joining portions. These modified interconnecting portions 6' are located in a plane perpendicular to the main direction of the body passage and by arranging a number of these ring-shaped structures along the stent, the flexibility of the stent in the longitudinal direction is thereby increased. The support of the body passage wall remains more or less unchanged for a longer time due to the remaining smaller parts. The distances between the ring-shaped structures of joining portions influence the sizes of the smaller parts into which the stent initially degrades. These remaining smaller parts may then have an essentially cylindrical shape, but they may also be more or less ring-shaped.

FIGS. 6b and 6c illustrate the third embodiment with no modified interconnecting portions where the joining portions just have been dissolved (FIG. 6b) and where the structure of the interconnecting portions 6 of the stent is more or less broken (FIG. 6c).

According to a preferred alternative of this third embodiment the joining portions are made from a said first material that is a resorbable polymer.

Although illustrated as essentially being straight the interconnecting portions may also have other shapes, e.g. being curve-shaped.

In this third embodiment the joining portions and interconnecting portions may also be made of different metals, a first metal and a second metal, respectively. These metals have different electrochemical potentials, thereby forming a galvanic element that drives an electrochemical process in which the first metal is consumed inside said body passage leaving the stent in smaller parts, which have cylindrical shapes or a ring shapes.

Figure 7A:
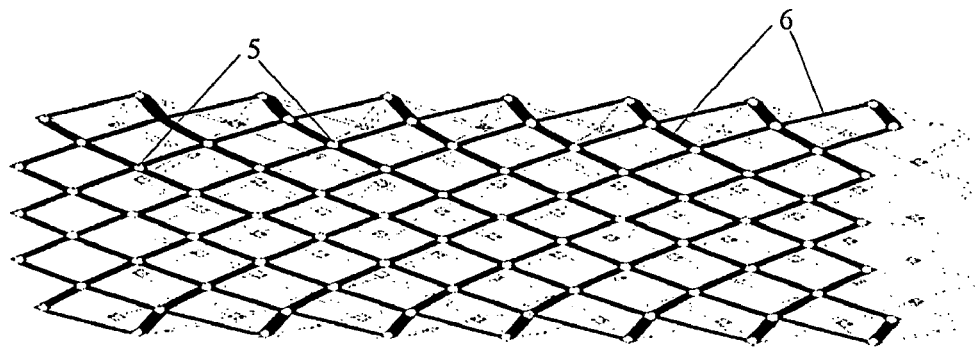
FIGS. 7a–7c illustrate a variant of the third embodiment of the present invention.
Figure 7B:
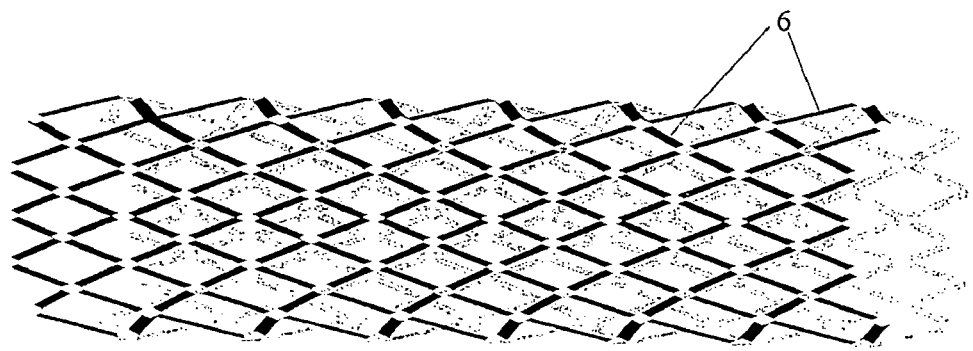
Figure 7C:
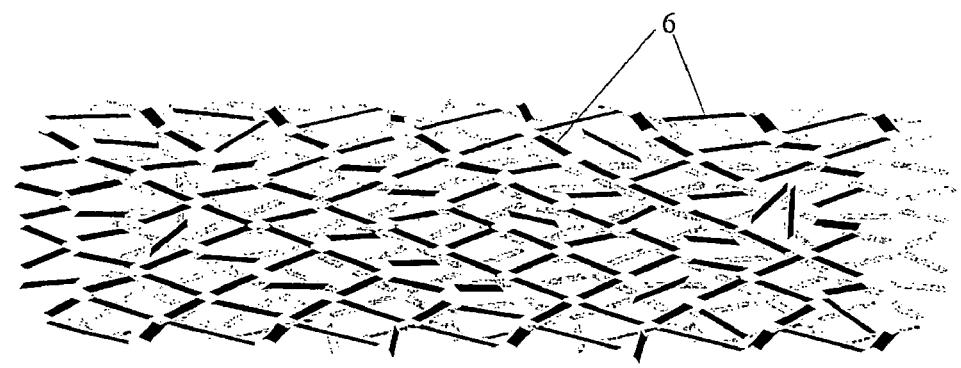

In FIGS. 7a–7c a stent having a mesh structure comprising quadratic or rectangular cells is illustrated. In FIG. 7a the stent, comprising interconnecting portions 6 and joining portions 5, is shown prior implantation, and in FIG. 7b the degrading procedure has come to the point where the joining portions have degraded but the interconnecting portions are left more or less unchanged. In the phase of the degrading procedure illustrated in FIG. 7c the remaining structure of the interconnecting portions of the mesh structure are beginning to be dissolved.

Figure 4:
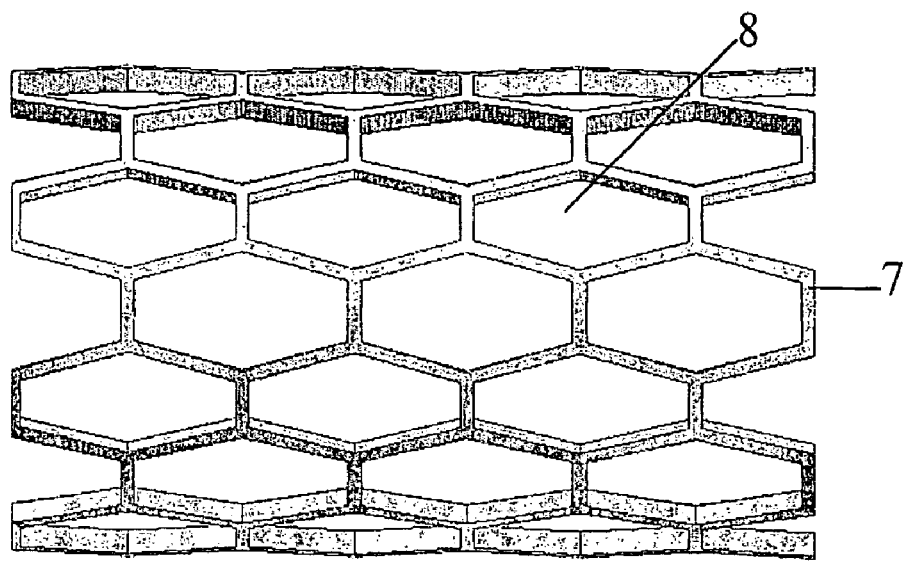
FIG. 4 shows a fourth embodiment of an expandable metal mesh stent according to the invention.
Figure 5:
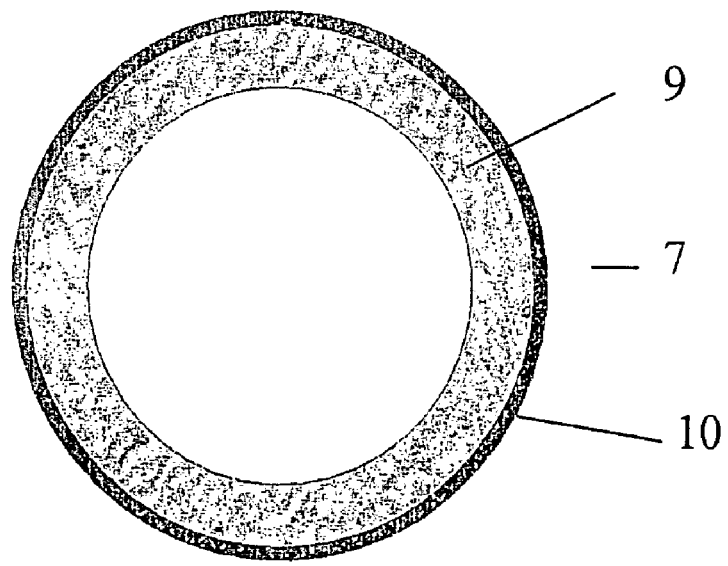
FIG. 5 shows a cross-section of the stent of FIG. 4.

The invention also relates to a method of manufacturing stents by direct laser cutting from a single metal tube. For the inventive purposes, this method could be applied on a tube made of two metals. FIG. 4 illustrates a stent 7, which has been laser-cut to a desired mesh structure 8. As is shown in cross-section in FIG. 5, the stent 7 is made from a metal tube comprising a first layer 9 of first metal, such as stainless steel, and a second layer 10 of a second metal, such as platinum, the second metal having a higher electrochemical potential than the first metal. For clarity of illustration, the two layers have been enlarged in FIG. 5. In practise, the second metal would have been applied as a very thin layer 10 on the outside of the tube. As an alternative, the second metal could be applied on the inside of the tube. With this configuration, laser cutting or other conventional manufacturing methods, such as etching, can be applied as for a stent made from a single metal tube. Furthermore, such a stent would exhibit essentially the same mechanical properties, as a stent made of the first metal only. The latter is, of course, only valid before and immediately after implantation in a vessel, i.e. before the start of any electrochemical process.

In this context, it should be noted that the normal corrosion process also is an electrochemical process, and if two or more metals are used in a stent, one (or all) of the metals will corrode and dissolve due to the normal corrosion mechanism, in addition to the corrosion driven by the galvanic element as described above. It should also be noted that it is possible to obtain "internal" galvanic elements if granules or small cells of a second metal are present in a first metal. The second metal may be present naturally in the first metal or may be implanted into the first metal by means of some suitable technique such as sintering. Obviously, the same effect would arise if the metal of which the stent is made comprises more than two metals with different electrochemical potentials. Such internal galvanic elements would accelerate the normal corrosion process and would also provide a further possibility to control the disintegration of the stent. With appropriate choice of metals, the same effect may also be utilized if an alloy or a compound of two or more metals is used for the manufacturing of the stents.

Finally, it should be noted that herein the term "expandable" encompasses both self-expanding and non-self-expanding mesh stents.

Although the present invention has been described with reference to specific embodiments, also shown in the appended drawings, it will be apparent for those skilled in the art that many variations and modifications can be done within the scope of the invention as described in the specification and defined in the following claims.

The invention claimed is:

1. An expandable stent for insertion into a body passage comprising:
    a mesh structure of interconnecting portions joined together by joining portions, wherein said stent, when inserted into said body passage, is adapted to dissolve into smaller parts, and wherein the joining portions dissolve faster than the interconnecting portions.

2. An expandable stent according to claim 1, wherein: the joining portions are made from a first material and the interconnecting portions are made from a second material different from said first material, and wherein the first material dissolves faster than said second material.

3. An expandable stent according to claim 2, wherein: said first material is a resorbable polymer.

4. An expandable stent according to claim 1, wherein: the mesh structure makes the stent to dissolve in such a way that the longitudinal structural integrity initially is decreased.

5. An expandable stent according to claim 4, wherein: the longitudinal structural integrity decreases faster than the radial structural integrity decreases.

6. An expandable stent according to claim 5, wherein: the radial structural integrity is related to the forces exerted by the stent towards the body passage wall.

7. An expandable stent according to claim 1, wherein: said smaller parts have an essentially cylindrical shape.

8. An expandable stent according to claim 1, wherein: said smaller parts are essentially ring-shaped.

9. An expandable stent according to claim 1, wherein: said interconnecting portions are straight.

10. An expandable stent according to claim 1, wherein: said interconnecting portions are curve-shaped.

11. An expandable stent according to claim 1, wherein: said joining portions are made of metal.

12. An expandable stent according to claim 1, wherein: said interconnecting portions are made of metal.

13. An expandable stent according to claim 1, wherein: said joining portions and interconnecting portions are made of different metals, a first metal and a second metal, respectively.

14. An expandable stent according to claim 13, wherein: said first and second metals have different electrochemical potentials, thereby forming a galvanic element that drives an electrochemical process in which the first metal is consumed inside said body passage.

15. An expandable stent according to claim 14, wherein: the first metal is consumed in said electrochemical process after a pre-defined time inside said body passage.

16. An expandable stent according to claim 14, wherein: the second metal dissolves by corrosion inside said body passage.

17. An expandable stent according to claim 14, wherein: the second metal dissolves by corrosion after a pre-defined time inside said body passage.

18. An expandable stent according to claim 13, wherein: the second metal is provided as a thin layer on selected parts of the first metal.

19. An expandable stent according to claim 13, wherein: the first metal and the second metal are in the form of an alloy or a compound.

20. An expandable stent according to claim 1, wherein: the stent comprises more than two metals, all of which have different electrochemical potentials, thereby forming galvanic elements that each drives a respective electrochemical process in which the metal having the lower electrochemical potential is consumed.

21. An expandable stent according to claim 1, wherein: the joining portions and the interconnecting portions are made from the same material.

22. An expandable stent according to claim 21, wherein: said material is a metal.

23. An expandable stent according to claim 22, wherein: said metal dissolves by corrosion inside said body passage.

24. An expandable stent according to claim 22, wherein: said metal dissolves by corrosion after a pre-defined time inside said body passage.

25. An expandable stent according to claim 21, wherein: the joining portions have a higher porosity compared to the interconnecting portions.

26. An expandable stent according to claim 21, wherein: joining portions have a smaller radial thickness as compared to the radial thickness of the interconnecting portions.

27. An expandable stent according to claim 1, wherein: said stent comprises a first metal and a second metal.

28. An expandable stent according to claim 27, wherein: said first and second metals have different electrochemical potentials, thereby forming a galvanic element that drives an electrochemical process in which the first metal is consumed inside said body passage.

29. An expandable stent according to claim 28, wherein: the second metal is provided as a thin layer on the first metal.

30. An expandable stent according to claim 28, wherein: the second metal is provided as granules or cells within the first metal.

31. An expandable stent according to claim 28, wherein: the first metal is consumed in said electrochemical process after a pre-defined time inside said body passage.

32. An expandable stent according to claim 28, wherein: the second metal dissolves by corrosion inside said body passage.

33. An expandable stent according to claim 28, wherein: the second metal dissolves by corrosion after a pre-defined time inside said body passage.

34. An expandable stent according to claim 28, wherein: the second metal is provided as a thin layer on selected parts of the first metal.

35. An expandable stent according to claim 28, wherein: the second metal is provided at selected parts of the first metal.

36. An expandable stent according to claim 28, wherein: the first metal and the second metal are in the form of an alloy or a compound.

37. A method for the manufacturing of an expandable metal stent for insertion into a body passage, comprising the steps of:

providing a tube of a first metal, the outer surface and/or the inner surface of the tube being coated with a layer of a second metal, the second metal having an electrochemical potential that differs from the electrochemical potential of the first metal; and making an expandable metal stent from the tube, the stent having a mesh structure of interconnecting portions joined together by joining portions, said stent, when inserted into said body passage, adapted to dissolve into smaller parts, wherein the joining portions dissolve faster than the interconnecting portions.

38. A method according to claim 37, wherein: the tube, which is made of the first metal, is coated with layers of several metals, all of which have different electrochemical potentials.

39. A method according to claim 37, wherein: said manufacturing involves laser cutting or etching.

\* \* \* \* \*